United States Patent [19]

Mase et al.

[11] Patent Number: 4,948,795

[45] Date of Patent: Aug. 14, 1990

[54] PYRIDYLTHIAZOLIDINE CARBOXAMIDE DERIVATIVES AND THEIR INTERMEDIATES AND PRODUCTION OF BOTH

[75] Inventors: Toshiyasu Mase, Chiba; Hiromu Hara, Saitama; Toshimitsu Yamada, Ibaraki, all of Japan

[73] Assignee: Yamanouchi Pharmaceutical Co., Ltd., Tokyo, Japan

[21] Appl. No.: 337,064

[22] Filed: Apr. 12, 1989

[30] Foreign Application Priority Data

Apr. 28, 1988 [JP] Japan ................... 63-108743

[51] Int. Cl.$^5$ ................... A61K 31/495; A61K 31/44; C07D 401/14
[52] U.S. Cl. ................... 514/252; 514/227.8; 514/235.8; 514/241; 544/58.1; 544/58.4; 544/60; 544/121; 544/215; 544/295; 544/357; 544/364
[58] Field of Search ................... 544/364, 60, 121, 215, 544/295, 357, 58.1, 58.4; 514/252, 227.8, 235.8, 241, 256

[56] References Cited

U.S. PATENT DOCUMENTS 4,634,709  1/1987  Lasslo et al. ................... 544/364
4,737,500  4/1988  Sorg ................... 544/364

FOREIGN PATENT DOCUMENTS 279681  8/1988  European Pat. Off. ............ 544/364

OTHER PUBLICATIONS

Mase et al., Chem. Abst. 110-32877v (1989).
Fabre et al., Chem. Abst. 101-230510z (1984).
Braguet, Chem. Abst. 103-189808d (1985).
Jaeggi et al., Chem. Abst. 105-79165a (1986).

*Primary Examiner*—Cecilia Shen
*Attorney, Agent, or Firm*—Burgess, Ryan & Wayne

[57] ABSTRACT

This invention provides pyridylthiazolidine carboxamide derivative shown by general formula (I) and pharmaceutically acceptable salts thereof:

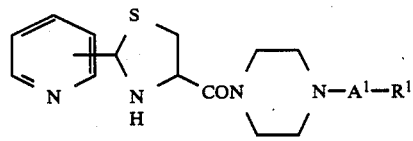

wherein $A^1$ is a single bond, carbonyl group or lower alkylene group which may include a carbonyl group and $R^1$ is a heterocyclic ring which may be substituted with a lower alkyl group and further provides N-substituted piperazine derivatives useful as intermediates for preparing said compounds (I).

10 Claims, No Drawings

PYRIDYLTHIAZOLIDINE CARBOXAMIDE DERIVATIVES AND THEIR INTERMEDIATES AND PRODUCTION OF BOTH

BACKGROUND OF THE INVENTION

FIELD OF THE INVENTION

This invention relates to novel pyridylthiazolidine carboxamide derivatives and salts thereof which have platelet activating factor (PAF) antagonizing activity and further relates to their intermediates.

DESCRIPTION OF THE RELATED ART

PAF is a chemical substance released from human and other animal cells and is an acetylglyceryl ether of phosphorylcholine as represented by the following formula:

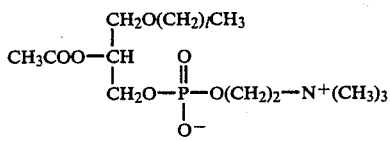

wherein l is the integer 15 or 17.

PAF is physiologically active and causes contraction of the airway smooth muscle, increased vascular permeation, platelet aggregation and blood pressure fall and the like. It is thought to be a factor inducing asthma, inflammation, thrombosis, shock and other symptoms. Therefore, studies of substances capable of antagonizing the physiological activities of PAF are underway and several anti-PAF agents have been reported (e.g. European patent application No. 178,261 (A), U.S. Pat. Nos. 4,539,332, 4,656,190 and 4,621,038, European patent No. 115,979 (B) and British patent application No. 2,162,062 (A)).

The present inventors found that novel pyridylthiazolidine carboxamide derivatives differing in chemical structure from the known anti-PAF agents have an excellent anti-PAF activity and that novel N-substituted piperazine derivatives are useful as intermediates for preparing the pyridylthiazolidine carboxamide derivatives afore-mentioned. Based on this finding the inventors have now completed the present invention.

SUMMARY OF THE INVENTION

The pyridylthiazolidine carboxamide derivatives of the present invention are shown by the following general formula (I):

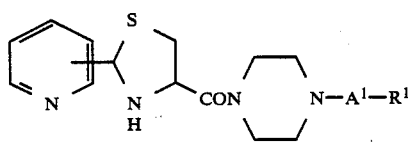

In the above formula (I), $A^1$ represents a single bond, a carbonyl group or a lower alkylene group which may contain a carbonyl group and $R^1$ represents a heterocyclic group which may be substituted by a lower alkyl group.

Further, the N-substituted piperazine derivatives useful as the intermediates are shown by the following general formula (II):

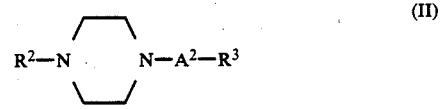

In the above formula (II), $A^2$ represents a lower alkylene group which may contain a carbonyl group; $R^2$ represents a hydrogen atom or an amino-protecting group and $R^3$ represents a heterocyclic group (except a pyridyl group) which may be substituted with a lower alkyl group.

The compounds of the present invention are described in more detail hereinbelow.

DETAILED DESCRIPTION OF THE INVENTION

In the definitions of the substituents used herein in the general formulas, the term "lower" means, unless othewise specified, a straight or branched carbon chain containing 1 to 6 carbon atoms.

Accordingly, the "lower alkyl group" specifically includes, among others, methyl, ethyl, propyl, isopropyl, butyl, isobutyl, sec-butyl, tertbutyl, pentyl (amyl), isopentyl, neopentyl, tertpentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl 1-ethyl-2-methylpropyl group, etc.

The "lower alkylene group which may contain a carbonyl group" represented by $A^1$ means both the "lower alkylene group" and the "lower alkylene group which contains a carbonyl group". The "lower alkylene group" represents a straight or branched alkylene group having 1 to 6 carbon atoms and specifically includes methylene, ethylene, trimethylene, methylmethylene, propylene, tetramethylene, 1-methyltrimethylene, 2-methyltrimethylene, 3-methyltrimethylene, ethylethylene, 1,2-dimethylethylene, 1,1-dimethylethylene, 2,2-dimethylethylene, propylmethylene, pentamethylene, 1-methyltetramethylene, 2-methyltetramethylene, 3-methyltetramethylene, 4-methyltetramethylene, 1,1-dimethyltrimethylene, 1,2-dimethyltrimethylene, 2,2-dimethyltrimethylene, 2,3-dimethyltrimethylene, 1,3-dimethyltrimethylene, 3,3-dimethyltrimethylene, 1-ethyltrimethylene, 2-ethyltrimethylene, 3-ethyltrimethylene, 1,1,2-trimethylethylene, 1,2,2-trimethylethylene, 1-ethyl-1-methylethylene, 1-ethyl-2-methylethylene, 2-ethyl-1-methylethylene, 2-ethyl-2-methylethylene, 1-propylethylene, 2-propylethylene, butylmethylene, hexamethylene, 1-methylpentamethylene, 2-methylpentamethylene, 3-methylpentamethylene, 4-methylpentamethylene, 5-methylpentamethylene group and the like.

The "lower alkylene group which contains a carbonyl group" is a straight or branched oxoalkylene group and specifically includes 2-oxoethylene ($-CH_2CO-$), 1-oxoethylene ($-COCH_2-$), 3-oxotrimethylene ($-CH_2CH_2CO-$), 2-oxotrimethylene ($-CH_2COCH_2-$), 1-oxotrimethylene ($-COCH_2CH_2-$), 1-methyl-2-oxoethylene ($-CH(CH_3)CO-$), 2-methyl-1-oxoethylene ($-COCH(CH_3)-$), 4-oxotetramethylene ($-CH_2CH_2CH_2CO-$), 3-oxotetramethylene ($-CH_2CH_2COCH_2-$), 2-oxotetramethylene ($-CH- $_2COCH_2CH_2$—), 1-oxotetramethylene (—COCH$_2$CH$_2$CH$_2$—), 1-methyl-3-oxotrimethylene (—CH(CH$_3$)CH$_2$CO—), 2-methyl-3-oxotrimethylene (—CH$_2$CH(CH$_3$)CO—), 1,1-dimethyl-2-oxoethylene (—C(CH$_3$)$_2$CO—), 1-ethyl-2-oxoethylene (—CH(C$_2$H$_5$)CO—), 3-methyl-1-oxotrimethylene (—COCH$_2$CH(CH$_3$)—), 2-methyl-1-oxotrimethylene (—COCH(CH$_3$)CH$_2$—), 2,2-dimethyl-1-oxoethylene (—COC(CH$_3$)$_2$—), 2-ethyl-1-oxoethylene (—COCH(C$_2$H$_5$)—), 5-oxopentamethylene (—CH$_2$CH$_2$CH$_2$CH$_2$CO—), 1-oxopentamethylene (—COCH$_2$CH$_2$CH$_2$CH$_2$—), 6-oxohexamethylene (—CH$_2$CH$_2$CH$_2$CH$_2$CH$_2$CO—), 1-oxohexamethylene (—COCH$_2$CH$_2$CH$_2$CH$_2$CH$_2$—) group and the like.

The "heterocyclic group" represented by R$^1$ is a saturated or unsaturated, heteromono- or hetero-polycyclic ring which contains 1 to 3 oxygen, sulfur and/or nitrogen atoms as heteroatoms. Among others, the 5- or 6-membered heteromonocyclic group which contains 1 to 3 oxygen, sulfur and/or nitrogen atoms as heteroatoms is preferable.

Accordingly, the preferable heterocyclic group is, for example, a 1 to 3 nitrogen atom-containing saturated or unsaturated, 5- or 6-membered heteromonocyclic group such as pyrrolyl ( 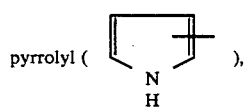 ), but this group may bind at the nitrogen atom of the ring, in this case it is shown by

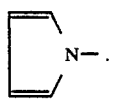

Hereinafter, the heterocyclic group having at least one non-tertiary nitrogen atom as heteroatoms may have the same form as above), pyrrolinyl ( 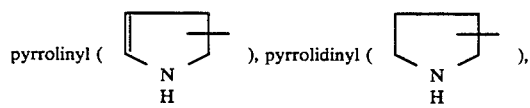 ), pyrrolidinyl ( ), pyridyl ( 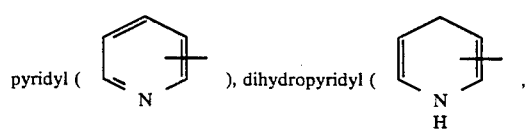 ), dihydropyridyl ( ),

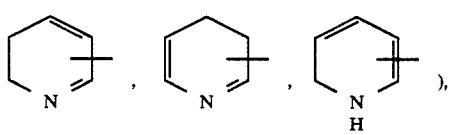

piperidinyl ( 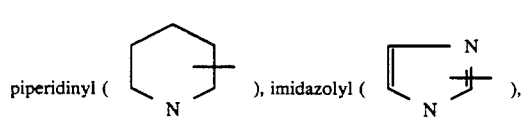 ), imidazolyl ( ),

-continued imidazolinyl ( 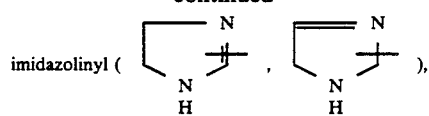 , ), imidazolidinyl ( 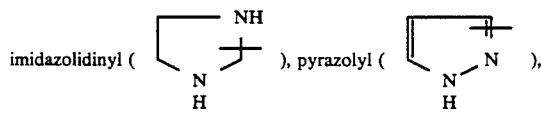 ), pyrazolyl ( ), pyrazolinyl ( 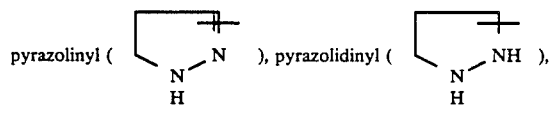 ), pyrazolidinyl ( ), pyrimidinyl ( 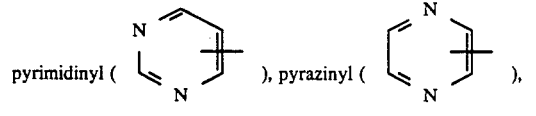 ), pyrazinyl ( ), piperazinyl ( 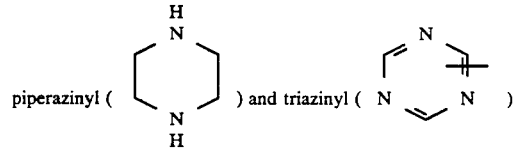 ) and triazinyl ( )

group; a 1 to 2 oxygen atoms-containing saturated or unsaturated, 5- or 6-membered heteromonocyclic group such as furyl ( 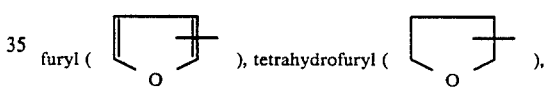 ), tetrahydrofuryl ( ), pyranyl ( 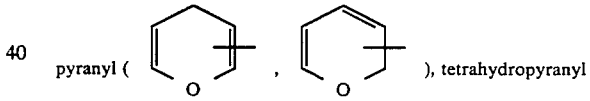 , ), tetrahydropyranyl ( 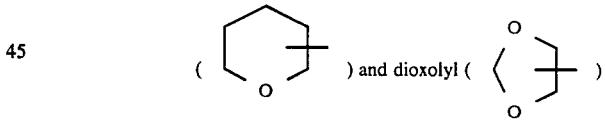 ) and dioxolyl ( )

group; a sulfur atom-containing saturated or unsaturated, heteromonocyclic group such as thienyl ( 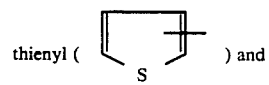 ) and tetrahydrothienyl ( 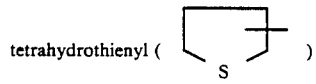 )

group; an oxygen and nitrogen atom-containing saturated or unsaturated, heteromonocyclic group such as oxazolyl ( 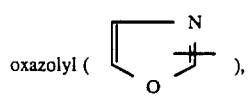 ),

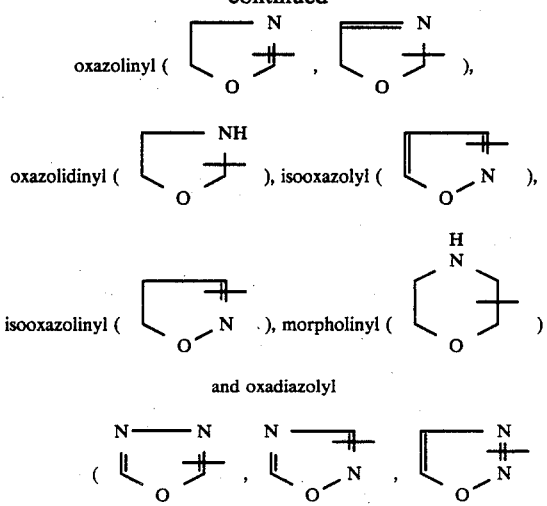

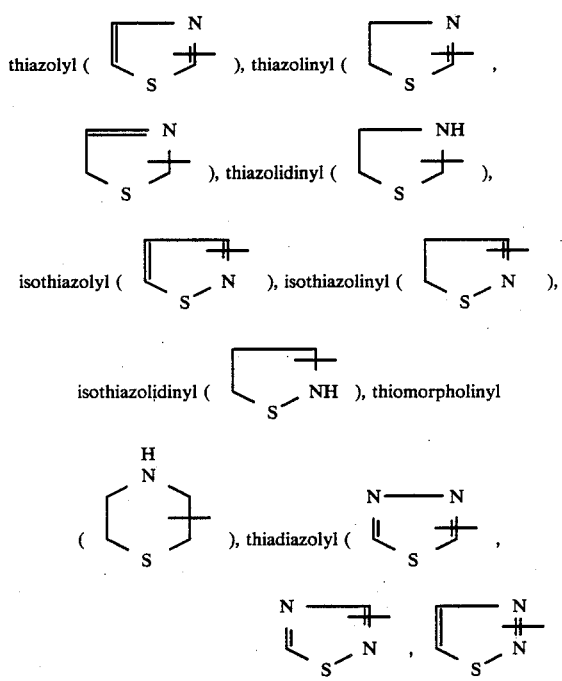

group and a sulfur and nitrogen atoms-containing saturated or unsaturated, heteromonocyclic group such as group and the like. These groups may be substituted with a lower alkyl group aforementioned.

The "lower alkylene group which may contain a carbonyl group" represented by $A^2$ may be the same group as the "lower alkylene group which may contain a carbonyl group" represented by $A^1$.

Examples of the amino-protecting group represented by $R^2$ are specifically an urethane type protective group such as a benzyloxycarbonyl type protective group, for example, benzyloxycarbonyl (carbobenzoxy), p-methoxybenzyloxycarbonyl, p-nitrobenzyloxycarbonyl, 3,5-dimethoxybenzyloxycarbonyl and 3,4,5-trimethoxybenzyloxycarbonyl group and an alkyloxycarbonyl type protective group, for example, tert-butoxycarbonyl, tert-amyloxycarbonyl, p-biphenylisopropyloxycarbonyl, diisopropylmethyloxycarbonyl and adamantyloxycarbonyl group; an acyl type protective group such as formyl, trifluoroacetyl, phthalyl, tosyl (toluenesulfonyloxy), o-nitrophenylsulfenyl, p-methoxyo-nitrophenylsulfenyl, benzoyl, chloroacetyl and acetoacetyl group; an alkyl type protective group such as trityl, benzhydryl, benzyl and trimethylsilyl group; an allylidene type protective group such as benzylidene and 2-hydroxyallylidene group and the like.

The "heterocyclic ring" represented by $R^3$ means the same group as the heterocyclic group, except the pyridyl group, represented by $R^1$.

The compounds (I) according to the present invention can form salts. The scope of the invention includes salts of the compounds (I). Such salts include acid addition salts with inorganic acids such as hydrochloric acid, sulfuric acid, nitric acid, phosphoric acid, hydrobromic acid and hydroiodic acid and with organic acids such as acetic acid, oxalic acid, succinic acid, citric acid, maleic acid, malic acid, fumaric acid, tartaric acid, picric acid, methanesulfonic acid and ethanesulfonic acid; salts with acidic amino acids such as glutamic acid and aspartic acid; quaternary ammonium salts resulting from quaternarization with alkyl halides such as methyl chloride, methyl bromide and methyl iodide, and so forth.

The compounds (I) provided by the present invention have at least two asymmetric carbon atoms and there can exist isomers due to such carbon atoms. Such isomers fall within the scope of the present invention either in each individual separated form or in a mixture form.

The compounds (I) according to the invention can be produced by applying various synthetic methods taking advantage of the characteristics of the skeletal structure and various substituents. Typical examples of applicable production processes are given below.

Process 1 (Amidation A)

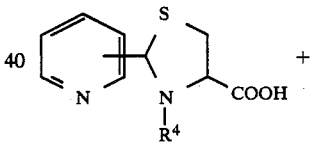

(III) or its reactive derivative

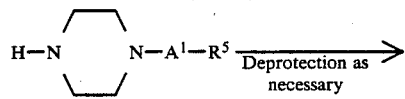

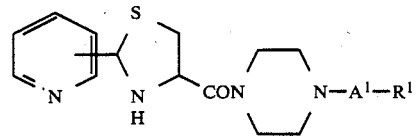

Process 2 (Amidation B)

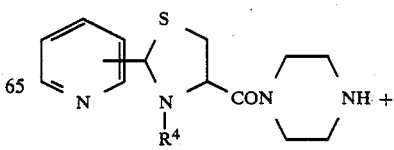

-continued

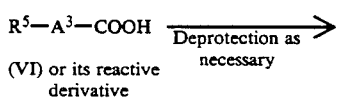
(VI) or its reactive derivative

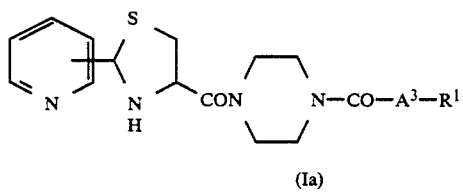
(Ia)

Process 3 (Amidation C)

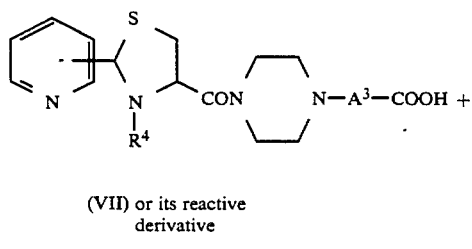
(VII) or its reactive derivative

H—N  B   →(Deprotection as necessary)

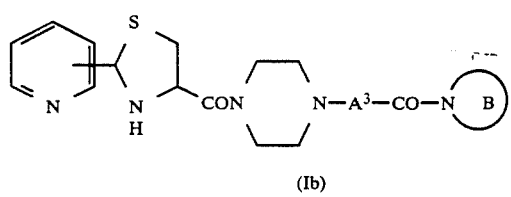
(Ib)

Process 4 (Cyclization)

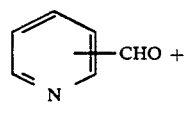
(IX)

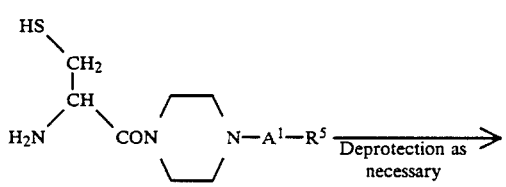
(X)

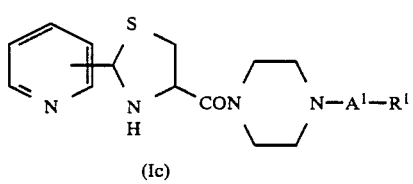
(Ic)

Process 5 (N-Alkylation A)

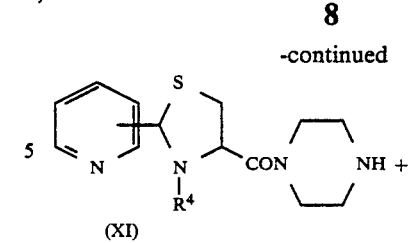
(XI)

$R^5-A^4-X$ →(Deprotection as necessary)
(XII)

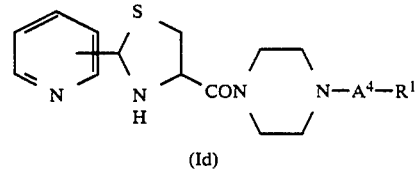
(Id)

Process 6 (N-Alkylation B)

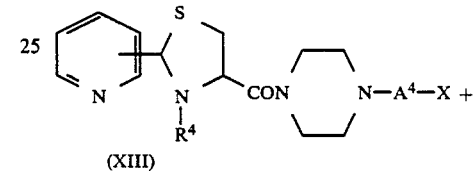
(XIII)

H—N  B   →(Deprotection as necessary)
(XIV)

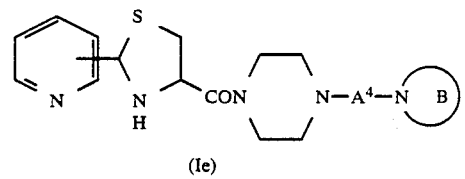
(Ie)

In the above reaction formulas, $A^1$ and $R^1$ are defined as above and the other substituents are defined as follows:

$R^4$: a hydrogen atom or an amino-protecting group;
$R^5$: the same group as $R^1$ which may have an amino-protecting group;
$A^3$: a single bond or a lower alkylene group;

HN⟨B⟩ a heterocyclic group containing one or more non-tertiary nitrogen atoms;
X: a halogen atom or an organic sulfonic acid residue; and
$A^4$: the same group as $A^1$ where the X-end is not a carbonyl group.

As the amino-protecting group represented by $R^4$, there may be mentioned the same group as the amino-protecting group represented by $R^2$. Also, the lower alkylene group represented by $A^3$ may be mentioned the same group as that having 1 to 5 carbon atoms in the lower alkylene group represented by $A^1$. The "one or more non-tertiary nitrogen atoms-containing heterocyclic group" means a heterocyclic group having at least one nitrogen atom as a hetero-atom where at least one nitrogen atom is not tertiary, among the heterocyclic groups represented by $R^1$, and preferably includes

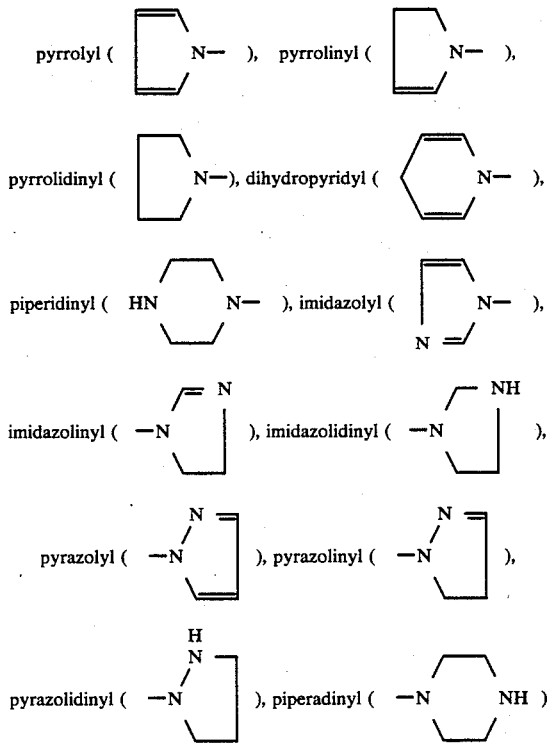

and the like.

Examples of a halogen atom represented by X are an iodine, bromine, chlorine atom, etc., and examples of the organic sulfonic acid residue include a lower alkylsulfonyloxy group such as methanesulfonyloxy, ethanesulfonyloxy, etc. and an aromatic sulfonyloxy group such as benzenesulfonyloxy, toluene (especially p-toluene) sulfonyloxy, etc.

The production processes are described in more detail hereinbelow.

Process 1

The compound (I) of the present invention can be produced by reacting a thiazolidine carboxylic acid shown by general formula (III) or a reactive derivative thereof with a 4-substituted piperazine represented by general formula (IV) or a salt thereof.

As the reactive derivative of compound (III), there may be mentioned acid halides such as acid chloride and acid bromide; acid azides; active esters with N-hydroxybenzotriazole or N-hydroxysuccinimide; symmetric acid anhydrides; mixed acid anhydrides with alkylcarbonic acids or p-toluenesulfonic acid and the like.

When the compound (III) is reacted in the free carboxylic acid form, it is advantageous to carry out the reaction in the presence of a condensing agent such as dicyclohexylcarbodiimide or 1,1'-carbonyldiimidazole.

The reaction conditions may vary to some extent depending on a starting compound, particularly on the kind of reactive derivatives of compound (III). Generally, however, it is advantageous to carry out the reaction in an organic solvent inert to the reaction, such as pyridine, tetrahydrofuran, dioxane, ether, N,N-dimethylformamide, benzene, toluene, xylene, methylene chloride, dichloroethane, chloroform, ethyl acetate, acetonitrile and the like, using the starting compounds of (III) and (IV) in equimolar amounts or one of them in excess.

According to the kind of reactive derivatives, or when the starting compound (IV) is used in a salt form, it is in some instances advatageous to carry out the reaction in the presence of a base, for example, an organic base such as trimethylamine, triethylamine, pyridine, picoline, lutidine, dimethylaniline and N-methylmorpholine or an inorganic base such as potassium carbonate, sodium carbonate, sodium hydrogen carbonate, sodium hydroxide and potassium hydroxide. It is also possible to promote the reaction by using the starting compound (IV) in excess. Pyridine may be also used as a solvent.

The reaction temperature may vary, hence should suitably be selected, depending on the kind of said reactive derivatives.

It is favorable in this reaction to use starting compounds where $R^4$ is not a hydrogen atom and $R^5$ is not a secondary ring amino group

It is possible, however, to use the compounds having such groups by means of protective group introduction prior to reaction and deprotection after reaction.

The method of deprotection, performed as necessary, can be carried out in conventional manner. For instance, the protection group such as benzyloxycarbonyl, benzyl, substituted benzyl, trityl, benzhydryl group, etc. is easily removed by catalytic reduction, the group such as tertbutoxycarbonyl, benzyloxycarbonyl group, etc. is by treatment with acids such as hydrobromic acid/acetic acid, hydrobromic acid trifluoroacetic acid, trifluoroacetic acid, hydrochloric acid/acetic acid, hydrochloric acid/dioxane, etc. and trimethylsilyl group is by contacting with water.

Process 2

The compound (Ia) of the present invention where $A^1$ is the group of the formula $-CO-A^3-$ can be produced by reacting a piperazinamide compound of the general formula (V) with a carboxylic acid (VI) or its reactive derivative of general formula (VI) and then carring out deprotection as necessary.

The reaction conditions and so forth of this process are substantially the same as in Process 1.

Process 3

The compound of the general formula (Ib) among the present invention compounds can be produced in substantially the same manner as in Process 1 using a carboxylic acid of the general formula (VII) or its reactive derivative and a cyclic amine of the general formula (VIII).

Process 4

The compound of the invention which has the general formula (Ic) can be produced by reacting a carbonyl compound of the general formula (IX) with a β-mercaptoamine of the general formula (X).

The reaction is carried out in the solvent of alcohols such as methanol, ethanol, isopropanol, etc. and of alcohols containing water, using the compounds (IX) and (X) in about equimolar amounts or one of them in excess generally at room temperature.

In respect of deprotection, this process is substantially the same as in Process 1.

Process 5

The compound of the general formula (Id) of the present invention can be produced by reacting a compound of the general formula (XI) with a compound of (XII), followed by deprotecting as necessary.

In the reaction using halide compounds as the starting compound of (XII), it is advantegeous to carry out the reaction in an organic solvent such as N,N-dimethylformamide, dimethylsulfoxide, acetone, methylethylketone (2-butanone), methanol, ethanol, methylenechloride, ethylenechloride, chloroform, ether, tetrahydrofuran, dioxane, etc., or water or in a mixed solvent thereof, using the starting compounds of (XI) and (XII) in about equimolar amounts or one of them in slight excess at room temperature, under heating or refluxing.

In this reaction, it is some instances advantageous to add a di- or tert-organic base such as pyridine, picoline, N,N-dimethylaniline, N-methylmorpholine, trimethylamine, triethylamine, dimethylamine, etc. or an inorganic base such as potassium carbonate, sodium carbonate, sodium hydrogen carbonate, sodium hydroxide, potassium hydroxide, etc. to proceed the reaction smoothly.

In the reaction using the compounds with an organic sulfonic acid residue as the starting compound (XII), it is advantageous to perform the reaction in the same solvent as in the process using the halide compounds afore-mentioned, using the starting compounds (XI) and (XII) in equimolar amounts or one of them in slight excess and under cooling or at room temperature.

The reaction time of this reaction may be suitably selected taking various kinds of the reaction conditions into account. Deprotection of the amino-protecting group is the same as in Process 1.

Process 6

The compound (Ie) of the present invention can be produced by reacting a compound of the general formula (XIII) with a compound of the general formula (XIV), followed by deprotecting the amino-protecting group if necessary.

The reaction of this process can be carried out in the same manner as in Process 5.

The intermediate shown by the general formula (II) afore-mentioned can be produced by various synthetic processes. Typical Examples of applicable processes are described in detail below.

Process (a)

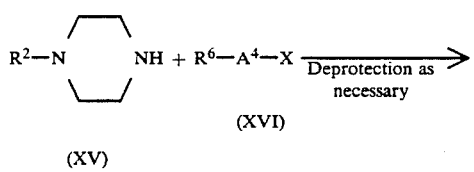

(XV)  (XVI)

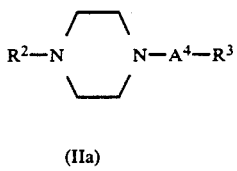

(IIa)

Process (b)

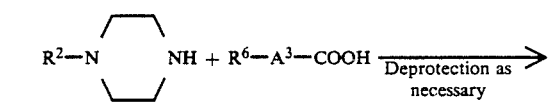

(XV)  (XVII) or its reactive derivative

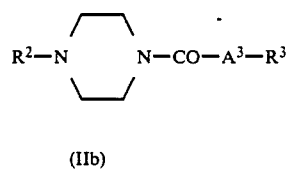

(IIb)

Process (c)

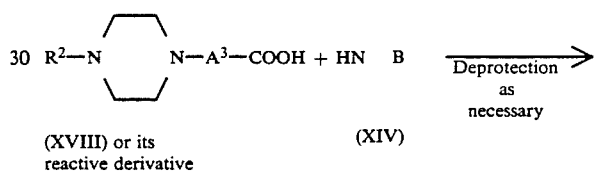

(XVIII) or its reactive derivative  (XIV)

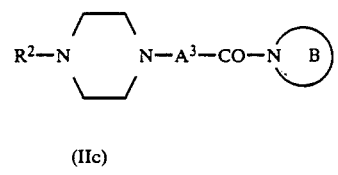

(IIc)

In the above formula$^e$, $R^2$, $R^3$, $A^3$, $A^4$ and

are defined as above, and $R^6$ represents the same meaning as $R^3$ which may have an amino-protecting group. As examples of the amino-protecting group, there may be mentioned the same groups as for $R^2$.

Process (a)

The intermediate compound (IIa) of the present invention can be produced by reacting a piperazine of (XV) with a halide or sulfonate compound.

The reaction can be carried out in the same manner as in Process 5.

When the amino-protecting group is employed in both $R^2$ and $R^6$, it is advantageous to select the same protective group and to deprotect simultaneously in one step. Deprotection may, of course, be carried out stepwise if the protective groups different in reactivity each other are used.

Process (b)

The intermediate shown by the general formula (IIb) can be produced by reacting the compound (XV) with a carboxylic acid of the general formula (XVII) or its reactive derivative.

In respect of kinds of the reactive derivative of the compound (XVII) and reaction conditions, the process is substantially the same as in Process 2. Also, the different protective groups may be employed as in Process (a).

Process (c)

The intermediate (IIc) can be produced by amidating the compound (XVIII) or its reactive derivative with the compound (XIV).

The reaction of this process is the same as in Process (b).

The resultant compounds (I) and intermediates (II) of the present invention are isolated in the free form or in the form of salts thereof and purified. The salts, as necessary, may be prepared by subjecting the free-form compounds to a conventional salt formation reaction.

Isolation and purification can be performed by applying ordinary procedures in chemistry, such as extraction, concentration, crystallization, filtration, recrystallization and various forms of chromatography.

As already mentioned hereinabove, the compounds (I) of the invention may occur as isomers such as racemic compounds, optically active isomers and diastereomers either singly or in the form of a mixture. Stereochemically pure isomers may be prepared by using appropriate starting compounds or by using a general method of optical resolution [e.g. the method which comprises conversion to diastereomer salts with an optically active acid in general use (e.g. tartaric acid)]. Separation of diastereomer mixtures can be realized in conventional manner, for example by fractional crystallization or chromatography.

The compounds (I) and salts thereof according to the invention have a PAF-antagonizing activity and are useful in the treatment and prevention of various diseases caused by PAF. In particular, they can be used as antiasthmatics, antiinflammatory agents, antiulcer agents, shock symptom alleviating agents, therapeutic agents for ischemic heart diseases, liver diseases, thrombosis and nephritis, rejection inhibitors for use in organ transplantation, etc.

Some of the compounds of the invention have vasodilating activity and such compounds are useful as vasodilators as well.

The anti-PAF activity of the compounds according to the invention has been confirmed by the following test:

EFFECT ON PLATELET ACTIVATING FACTOR (PAF)-INDUCED PLATELET AGGREGATION IN PLASMA

Method: Nine volumes of blood were drawn from the central ear artery of male rabbit (Japan white, 3 kg) directly into plastic syringe containing 1 volume of 3.8% sodium citrate. The blood was centrifuged at 270× g for 10 minutes and the platelet rich plasma (PRP) was removed. The pellet was further centrifuged at 1,100× g for 15 minutes. The supernatant was used as platelet poor plasma (PPP). PRP was adjusted to $5 \times 10^5$ cells/$\mu$l with PPP. PAF-induced platelet aggregation was measured by the method of G. V. R. Born and M. J. Cross [Journal of Physiology, 168, 178-195 (1963)]. That is the change of light transmission in PAF ($10^{-8}$)-induced PRP was measured using NBS HEMA TRACER (Nikou Bio Science, Japan). The test compound was added two minutes before addition of PAF. Percent inhibition with the compound was calculated by dividing the percent aggregation in the presence of the compound by that in the control, and then the IC$_{50}$ values were calculated. The compounds of Examples 6 and 5 were potent inhibitors having IC$_{50}$ values of $1.0 \times 10^{-7}$ and $2.5 \times 10^{-7}$M, respectively. These compounds did not inhibit the platlet aggregation induced by ADP (3 $\mu$M), arachidonic acid (100 $\mu$M) or collagen (10 $\mu$g/ml), and hence the results suggest that the compounds of this invention are specific antagonists of PAF.

The compound (I) or its non-toxic salt of the present invention can be orally or parenterally administered as it is or as a medical composition composed of this compound and a pharmaceutically acceptable carrier or excipient (e.g., tablets, capsules, powders, granules, pills, ointments, syrups, injections, inhalants, suppositories, etc.). The dose depends on patients to be administered, administration routes, symptoms, etc., but is usually 0.1 to 500 mg, preferably 1 to 200 mg per adult per day and is orally or parenterally administered in 2 or 3 sub-doses per day.

The compound represented by the general formula (II) is useful as the intermediate for production of the above-mentioned compound (I) of the invention which possesses excellent effects as a medical compound. That is, the compound (II), after deprotection if it has the protective group or as it is if it has no protective group, may be subjected to the reaction of Process 1.

The following examples are further illustrative of the present invention.

In the following, NMR indicates a nuclear magnetic resonance spectrum with TMS as an internal standard and MS indicates mass spectrum.

REFERENCE EXAMPLE 1

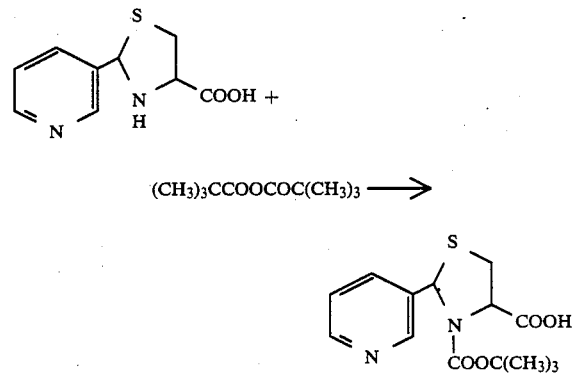

Di-tert-butyl dicarbonate (2.4 g) and 10 ml of 1N aqueous sodium hydroxide were added to a mixture of 2.1 g of 2-(3-pyridyl)thiazolidine-4-carboxylic acid, 20 ml of water and 40 ml of dioxane at a temperature not higher than 4° C., and the mixture was stirred at room temperature for 30 minutes. The reaction mixture was concentrated under reduced pressure, 30 ml of water was added, the pH was adjusted to 2 to 3 by addition of 0.5M aqueous citric acid, and the mixture was extracted with ethyl acetate. The extract was washed with water, dried over anhydrous sodium sulfate and concentrated under reduced pressure, and the residue was recrystallized from ethyl acetate to give 1 g of N-tert-butoxycarbonyl-2-(3-pyridyl)thiazolidine-4-carboxylic acid. Melting point 167° C.-169° C.

INTERMEDIATE EXAMPLE 1

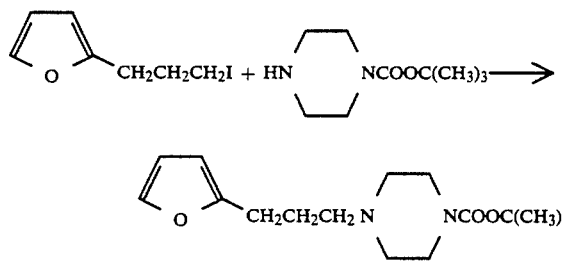

To a mixture of 1.16 g of 1-tert-butoxycarbonylpiperazine, 1.47 g of 2-(3-iodopropyl)furan and 20 ml of N,N-dimethylformamide was added 0.86 g of anhydrous potassium carbonate, and the mixture was stirred overnight at room temperature. To the reaction solution was added 300 ml of ethyl acetate, the solution was washed successively with water and saturated aqueous solution of sodium chloride, dried over anhydrous magnesium sulfate and concentrated under reduced pressure. The residue was subjected to column chromatography and eluted with ethyl acetate to give 1.5 g of oily 1-tert-butoxycarbonyl-4-[3-(2-furyl)propyl]piperazine.

NMR (CDCl$_3$) δ: 1.44(9H, s), 1.7–2.0(2H, m), 2.2–2.5 (6H, m), 2.66(2H, t), 3.3–3.6(4H, m), 5.9–6.1(1H, m), 6.2–6.4(1H, m), 7.2–7.4(2H, m).

MS: m/z 294 (M+).

INTERMEDIATE EXAMPLE 2

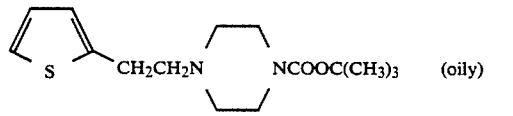

1-tert-butoxycarbonyl-4-[2-(2-thienyl)ethyl]piperazine was prepared in the same manner as in Intermediate Example 1.

NMR (CDCl$_3$) δ: 1.48(9H, s), 2.3–2.8(6H, m), 2.8–3.2 (2H, m), 3.3–3.6(4H, m), 6.8–7.4(3H, m).

MS: m/z 296 (M+).

INTERMEDIATE EXAMPLE 3

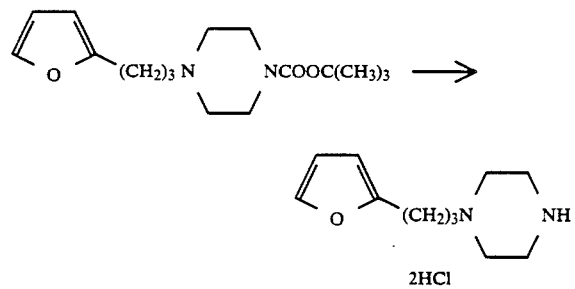

To 1.5 g of 1-t-butoxycarbonyl-4-[3-(2-furyl)propyl]-piperazine was added 5 ml of trifluoroacetic acid under ice-cooling, and the resultant mixture was stirred at room temperature for 2 hours. The reaction mixture was concentrated under reduced pressure, and then dissolved in ethyl acetate 10 ml. To the solution was added 4N hydrochloric acid-dioxane solution under ice-cooling to yield 1.3 g of 1-[3-(2-furyl)propyl]-piperazine.2 hydrochloride.

NMR (DMSO - d$_6$) δ: 1.7–2.4(2H, m), 2.5–2.9(2H, m), 3.0–3.8 (10H, m), 6.0–6.5(2H, m), 7.5–7.8(2H, m).

MS: m/z 184 (M+-2HCl).

INTERMEDIATE EXAMPLE 4

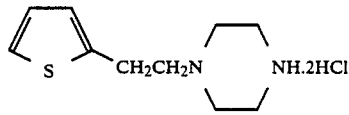

1-[2-(2-thienyl)ethyl]piperazine.2 hydrochloride was obtained in the same manner as in Intermediate Example 3.

NMR (DMSO - d$_6$) δ: 3.2–3.8(12H, m), 7.0(2H, d), 7.3–7.8(2H, m).

MS: m/z 197 (M+1-2HCl).

INTERMEDIATE EXAMPLE 5

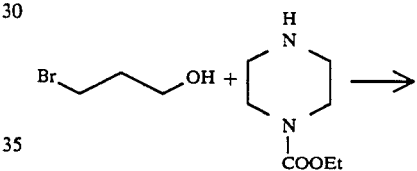

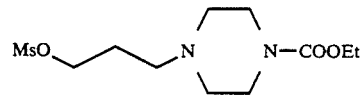

To a solution of 3-bromopropanol 4.17 g, ethyl 1-piperazinecarboxylate 4.74 g and 2-butanone 20 ml was added anhydrous potassium carbonate 4.74 g, followed by refluxing for 5 hours. After cooling, the reaction mixture was diluted with ethyl acetate 100 ml and water 50 ml. The organic layer was taken using a separating funnel and then dried over anhydrous magnesium sulfate. The solvent was distilled off under reduced pressure. The resultant residue was dissolved in dichloromethane 150 ml. To the solution were added 4-dimethylaminopyridine 6.21 g and methanesulfonylchloride 2.0 ml and the mixture stirred under ice-cooling for 3 hours. After adding water 50 ml to the reaction mixture, the organic layer was separated and after drying the solvent was distilled off under reduced pressure. The resultant residue was purified by using silica gel column chromatography (eluent: 2% methanol-ethyl acetate) to yield 4.76 g of 1-ethoxycarbonyl-4-(3-mesyloxypropyl)-piperazine.

NMR (CDCl$_3$) δ: 1.26(3H, t), 1.68–2.20(2H, m), 2.25–2.70 (6H, m), 3.02(3H, s), 3.34–3.68(4H, m), 3.92–4.50(4H, m).

INTERMEDIATE EXAMPLE 6

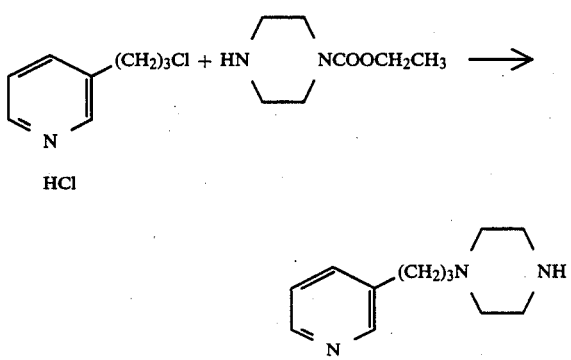

A mixed solution of 3-(3-chloropropyl)pyridine 1.92 g, ethyl 1-piperazinecarboxylate 1.6 g, anhydrous potassium carbonate 3.0 g, potassium iodide 1 g, tetra-n-butylammonium bromide 0.1 g and 2-butanone 50 ml was refluxed for 24 hours. To the reaction mixture was added water 50 ml, and the product was extracted with ethyl acetate. The extract was washed with saturated aqueous solution of sodium chloride, dried over anhydrous magnesium sulfate and concentrated to dryness under reduced pressure to yield 1-ethoxycarbonyl-4-[3-(3-pyridyl)propyl]piperazine. This was dissolved in a mixture of 20% sodium hydroxide 25 ml and ethanol 25 ml and the solution refluxed for 2 days. The reaction mixture was concentrated under reduced pressure and to the residue was added ethyl acetate 100 ml and anhydrous magnessium sulfate. After stirring the resultant mixture, the insoluble matter was filtered off. The filtrate was concentrated under reduced pressure to yield 1.56 g of oily 1-[3-(3-pyridyl)propyl]piperazine.

NMR (CDCl$_3$) δ: 1.6–2.0(2H, m), 2.2–2.5(6H, m), 2.66(2H, t), 7.1–7.3(1H, m), 7.4–7.6(1H, m), 8.3–8.6(2H, m).

MS: m/z 205 (M+).

INTERMEDIATE EXAMPLE 7

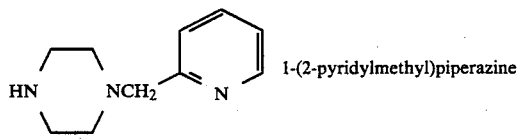

The compound of Intermediate Example 7 was obtained in the same manner as above.

NMR (CDCl$_3$) δ: 2.4–2.6(4H, m), 2.8–3.0(4H, m) 3.64(2H, s), 7.0–7.8(3H, m), 8.5–8.7(1H, m).

MS: m/z 177 (M+).

INTERMEDIATE EXAMPLE 8

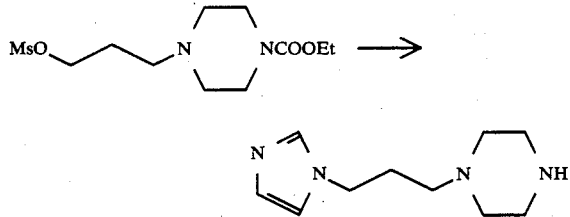

To a solution of imidazole 0.68 g and N,N-dimethylformamide 20 ml was added 60% sodium hydride 0.60 g under ice-cooling, followed by stirring at room temperature for 5 minutes. To the resultant mixture was added 1-ethoxycarbonyl-4-(3-mesyloxypropyl)piperazine 3.68 g and the mixture was stirred at room temperature overnight. To the reaction mixture were added saturated solution of sodium hydrogen carbonate 50 ml and ethyl acetate 200 ml and the organic layer was taken using a separating funnel, dried over anhydrous magnesium sulfate and the solvent distilled off under reduced pressure. The resultant residue was purified by silica gel column chromatography (eluent: 10% methanol-ethyl acetate), and dissolved in ethanol 25 ml. To the solution was added 10% sodium hydroxide 25 ml and the mixture refluxed overnight. After cooling, ethyl acetate 100 ml was added to the solution, the organic layer was separated, and the aqueous layer extracted with ethyl acetate. The organic layers were combined, dried over anhydrous sodium sulfate, and concentrated under reduced pressure to give 1.39 g of 1-[3-(1-imidazolyl)-propyl]piperazine.

NMR (CDCl$_3$) δ: 1.76–2.14(2H, m), 2.14–2.60(6H, m) 2.80–3.10(4H, m), 3.90–4.20(2H, m), 6.80–7.80(3H, m).

EXAMPLE 1

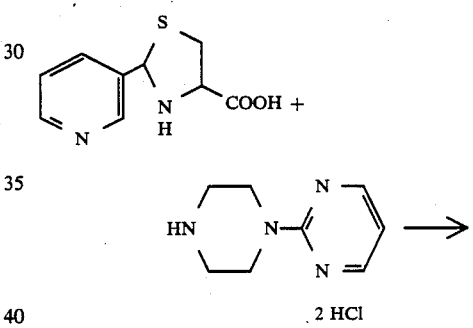

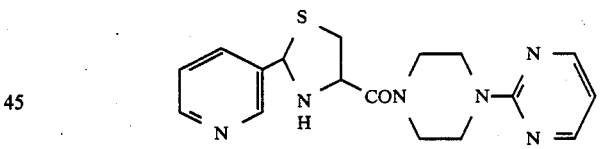

To a solution of 2-(3-pyridyl)thiazolidine-4-carboxylic acid 2.1 g, 1-(2-pyrimidinyl)piperazine.2 hydrochyloride 2.2 g, triethylamine 1.8 g, 1-hydroxybenzotriazole 1.5 g and N,N-dimethylformamide 30 ml was added dicyclohexylcarbodiimide 2.0 g under cooling and the mixture was stirred overnight at room temperature. The resultant dicyclohexylurea was distilled off, ethyl acetate 100 ml and water 50 ml were added to the filtrate and the solution was basified by addition of potassium carbonate. The organic layer was separated and the aqueous layer extracted with ethyl acetate. The organic layer and extract were combined, washed successively with water and saturated aqueous solution of sodium chloride, dried over anhydrous sodium sulfate and concentrated under reduced pressure. The residue was recrystallized from ethanol to give 0.8 g of 1-[2-(3-pyridyl)thiazolidine-4-ylcarbonyl]-4-(2-pyrimidinyl)-piperazine.

Melting point: 156°–159° C.

Elemental analysis (for C$_{17}$H$_{20}$N$_6$OS)

| | C (%) | H (%) | N (%) | S (%) |
|---|---|---|---|---|
| Calc. | 57.28 | 5.66 | 23.58 | 9.00 |
| Found | 57.52 | 5.70 | 23.37 | 8.87 |

EXAMPLE 2

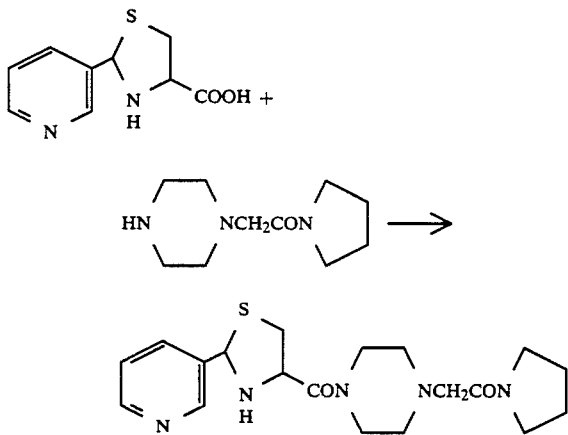

To a solution of 2-(3-pyridyl)thiazolidine-4-caroxylic acid 2.1 g, 1-(pyrrolidinecarbonylmethyl)piperazine 1.8 g, 1-hydroxybenzotriazole 1.5 g and N,N-dimethylformamide 50 ml was added dicyclohexylcarbodiimide 2 g under ice-cooling, and the mixture was stirred overnight at room temperature. The resultant dicyclohexylurea was filtered off and the filtrate concentrated under reduced pressure. To the residue were added ethyl acetate 100 ml and water 10 ml, the mixture was basified by addition of sodium carbonate, sodium chloride added until saturation and allowed to stand. The organic layer was separated, washed with saturated aqueous sodium chloride solution, dried over anhydrous sodium sulfate and concentrated under reduced pressure. The residue was subjected to silica gel column chromatography and eluted with a mixture solution of ethyl acetate - methanol (6:4) to give 2.1 g of 1-[2-(3-pyridyl)thiazolidine-4-ylcarbonyl]-4-[1-(pyrrolidinyl)-carbonylmethyl]piperazine.

NMR (CDCl₃) δ: 1.6–2.2(4H, m), 2.5–2.8(4H, m), 3.8(2H, s), 2.8–3.8(14H, m), 3.8–4.3(1H, m), 5.6, 5.98(jointly 1H, s,d), 7.16–7.42(1H, m), 7.7–8.0(1H, m), 8.4–8.66(1H, m), 8.6–8.80(1H, m).

MS: m/z 389 (M+).

EXAMPLE 3

The following compound was obtained in the same manner as in Example 2.

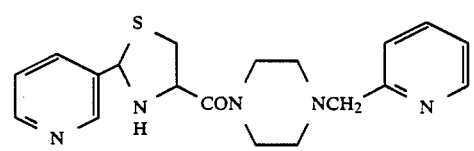

1-[(2-pyridyl)methyl]-4-[2-(3-pyridyl)thiazolidine-4-ylcarbonyl]piperazine

NMR (CDCl₃) δ: 2.4–2.8(4H, m), 2.8–4.0(8H, m), 4.0–4.4(1H, m), 5.5–6.1(1H, m), 7.0–7.5(3H, m), 7.5–8.0(2H, m), 8.4–8.8(3H, m).

MS: m/z 369 (M+).

EXAMPLE 4

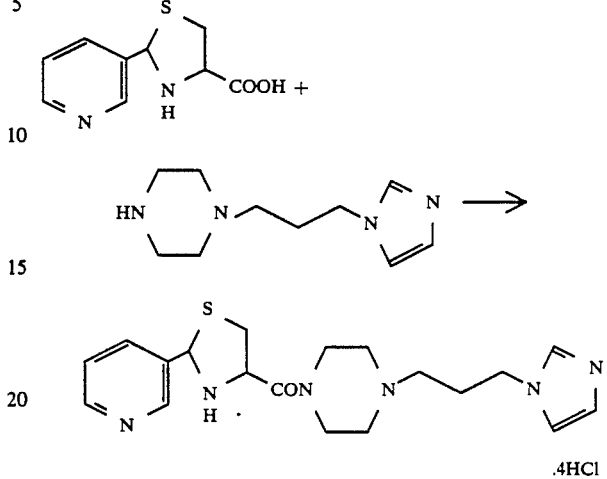

To a solution of 2-(3-pyridyl)thiazolidine-4-carboxylic acid 630 mg, 1-[3-(1-imidazolyl)propyl]piperazine 580 mg, 1-hydroxybenztriazole 410 mg and N,N-dimethylformamide 15 ml was added dicyclohexylcarbodiimide 620 mg under ice-cooling and then stirred overnight at room temperature. Ethyl acetate 100 ml was added to the solution, the resultant unsoluble matter filtered off and the solution washed with saturated aqueous solution of sodium hydrogen carbonate and saturated aqueous solution of sodium chloride in succession. After drying over anhydrous sodium sulfate, the solvent was distilled off under reduced pressure, ethyl acetate added to the residue, the unsoluble matter filtered off and the solution concentrated to dryness under reduced pressure. The residue thus obtained was subjected to silica gel column chromatography (eluent: 20% methanol - ethyl acetate) to give an oily product. This was dissolved in ethyl acetate 30 ml, 2N hydrogen chloride - dioxane 4 ml added and the precipitated powder filtered off to give 620 mg of 1-[3-(1-imidazolyl)propyl]-4-[2-(3-pyridyl)thiazolidine-4-ylcarbonyl]piperazine.4 hydrochloride.

Melting point: 152°–154° C.

Elemental analysis (for C₁₉H₃₀N₆OSCl₄.2H₂O)

| | C (%) | H (%) | N (%) | S (%) |
|---|---|---|---|---|
| Calc. | 40.15 | 6.03 | 14.79 | 5.64 |
| Found | 40.26 | 5.79 | 14.84 | 5.74 |

EXAMPLE 5

The following compound was obtained in the same manner as in Example 4.

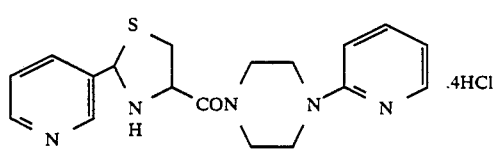

1-(2-pyridyl)-4-[2-(3-pyridyl)thiazolidine-4-ylcarbonyl]piperazine.4 hydrochloride Melting point: 147°–151° C.
Elemental analysis (for $C_{18}H_{25}N_5OSCl_4.1/2H_2O$)

|  | C (%) | H (%) | N (%) |
|---|---|---|---|
| Calc. | 42.37 | 5.14 | 13.72 |
| Found | 42.51 | 5.24 | 13.69 |

EXAMPLE 6

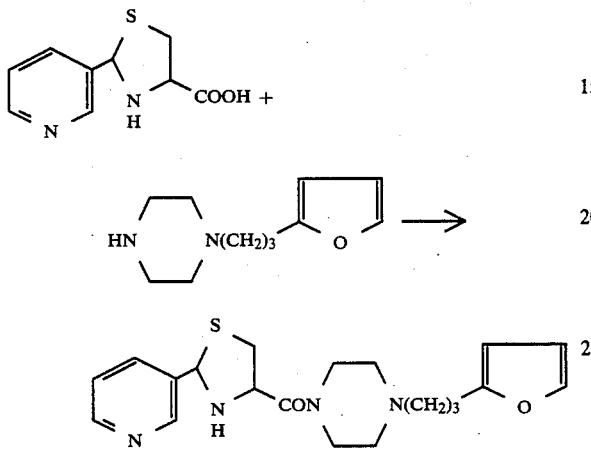

To a mixture solution of 2-(3-pyridyl)thiazolidine-4-carboxylic acid 0.5 g, 1-[3-(2-furyl)propyl]piperazine.2 hydrochloride 0.54 g and N,N-dimethylformamide 5 ml were added N-methylmorpholine 0.2 g and N,N-dimethylformamide 2 ml under ice-cooling. Further 1-hydroxybenzotriazole 0.4 g was added, then dicyclohexylcarbodiimide 0.46 g added and the mixture was stirred overnight at room temperature. Ethyl acetate 50 ml and water 10 ml were added, the solution basified with sodium hydrogen carbonate, the insoluble matter filtered off and the solution transferred into a separating funnel. The aqueous layer was extracted with ethyl acetate, the extract combined with the organic layer, washed with water and saturated aqueous sodium chloride solution, dried over anhydrous sodium sulfate and concentrated under reduced pressure. The residue was subjected to silica gel column chromatography and eluted with a mixture solution of ethyl acetate - methanol (4:1) to give 0.25 g of oily 1-[3-(2-furyl)-propyl]-4-[2-(3-pyridyl)thiazolidine-4-ylcarbonyl]piperazine.

NMR (CDCl$_3$) δ: 1.5–2.0(2H, m), 2.2–2.6(6H, m), 2.70(2H, t), 2.7–3.8(6H, m), 4.0–4.2(1H, m), 5.5–6.4(3H, m), 7.2–7.4(2H, m), 7.6–8.0(1H, m), 7.4–7.9(2H, m).

MS: m/z 386 (M+).

EXAMPLE 7

The following compound was prepared in the same manner as in Example 6.

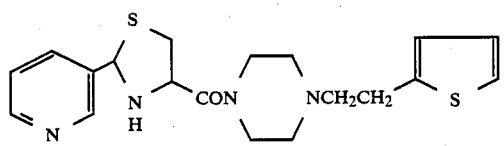

Oily 1-[2-(3-pyridyl)thiazolidine-4-ylcarbonyl]-4-[2-(2-thienyl)ethyl]piperazine.

NMR (CDCl$_3$) δ: 2.4–3.8(14H, m), 3.6–4.3(1H, m), 5.5–6.1(1H, m), 6.8–7.0(2H, m), 7.1–7.4(2H, m), 7.6–8.0(1H, m), 8.4–8.9(2H, m).

MS: m/z 388 (M+).

EXAMPLE 8

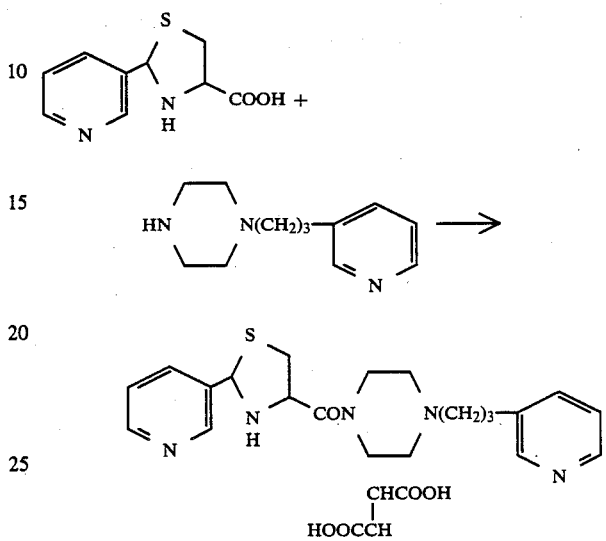

To a mixture solution of 2-(3-pyridyl)thiazolidine-4-carboxylic acid 1.7 g, 1-[3-(3-pyridyl)propyl]piperazine 1.56 g, 1-hydroxy-benzotriazole 1.3 g and N,N-dimethylformamide 20 ml was added dicyclohexylcarbodiimide 1.67 g under ice-cooling, and the mixture stirred overnight at room temperature. Ethyl acetate 50 ml was added, the precipitated dicyclohexylurea filtered off, water 30 ml added to the filtrate, the resultant solution basified with sodium hydrogen carbonate and transferred into a separating funnel. The aqueous layer was washed with ethyl acetate, the washings combined with the ethyl acetate layer, and the resultant ethyl acetate solution washed with water and saturated aqueous solution of sodium chloride, dried over anhydrous sodium sulfate and concentrated under reduced pressure. The residue was subjected to silica gel column chromatography and eluted with a mixture solution of ethyl acetate - methanol (4:1) to give 860 mg of oily 1-[3-(3-pyridyl)-propyl]-4-[2-(3-pyridyl)thiazolidine-4-ylcarbonyl]piperazine. This product was dissolved in ethanol 8 ml and after addition to stand to yield crystals. The crystals were filtered off and dried to give 580 mg of 1-[3-(3-pyridyl)propyl-4-[2-(3-pyridyl)thiazolidine-4-ylcarbonyl]piperazine.fumarate.

Melting point: 156°–158° C.
Elemental analysis (for $C_{25}H_{31}N_5O_5S$)

|  | N (%) | S (%) |
|---|---|---|
| Calc. | 13.64 | 6.24 |
| Found | 13.36 | 6.23 |

EXAMPLE 9

Tablet composition

| | |
|---|---|
| The compound obtained in Example 6 | 20 mg |
| Lactose | 57 mg |
| Corn starch | 38 mg |

-continued

| | |
|---|---|
| Hydroxypropylcellulose | 4 mg |
| Magnesium stearate | 1 mg |
| Total | 120 mg |

A homogeneous mixture is prepared from 20 g of the compound produced by Example 6, 57 g of lactose and 38 g of corn starch. Then, 40 g of 10% hydroxypropylcellulose solution is added and the mixture is subjected to wet granulation. The granules are forced through a sieve and then dried. One gram of magnesium stearate is added to the thus-obtained granulation product. After thorough mixing the mixture is formed into tablets using a tableting machine (die-punch size: 7 m/m, 5.6 R).

EXAMPLE 10

Capsule composition (per capsule)

| | |
|---|---|
| The compound obtained in Example 6 | 15 mg |
| Crystalline cellulose | 40 mg |
| Crystalline lactose | 144 mg |
| Magnesium stearate | 1 mg |
| Total | 200 mg |

A homogeneous mixture is prepared from 15 g of the compound obtained in Example 6, 40 g of crystalline cellulose, 144 g of crystalline lactose and 1 g of magnesium stearate and filled into No. 3 capsules using a capsule-filling machine.

EXAMPLE 11

Lyophilized preparation composition (per vial)

| | |
|---|---|
| The compound obtained in Example 6 | 1 mg |
| D-Mannitol | 50 mg |
| Total | 51 mg |

In 800 ml of water are dissolved 1 g of the compound obtained in Example 6 and 50 g of D-mannitol in that order. Water is added to make the whole volume 1 liter. This solution is aseptically filtered, then filled in 1-ml portions into vials, and lyophilized.

While the invention has been described in detail and with reference to specific embodiments thereof, it should be apparent to one skilled in the art that various changes and modifications can be made therein without departing from the spirit and scope of the present invention.

What is claimed is:

1. A pyridylthiazolidine carboxamide derivative represented by the Formula (I) or a pharmaceutically acceptable salt thereof:

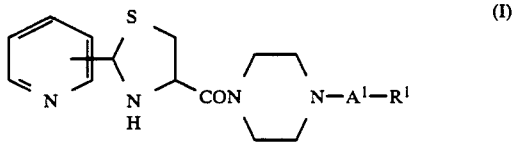

wherein A' represents a single bond, a carbonyl group or a lower alkylene group which may contain a carbonyl group and R' represents a 5- or 6-membered heterocyclic group containing 1 to 3 oxygen, sulfur or nitrogen atoms of heteroatoms, which may be substituted with a lower alkyl group.

2. A pyridylthiazolidine carboxamide derivative or a pharmaceutically acceptable salt thereof as claimed in claim 1 wherein $A^1$ represents a single bond.

3. A pyridylthiazolidine carboxamide derivative or a pharmaceutically acceptable salt thereof as claimed in claim 1 wherein $A^1$ represents a carbonyl group.

4. A pyridylthiazolidine carboxamide derivative or a pharmaceutically acceptable salt thereof as claimed in claim 1 wherein $A^1$ represents a lower alkylene group which may contain a carbonyl group.

5. A pyridylthiazolidine carboxamide derivative or a pharmaceutically acceptable salt thereof as claimed in claim 1 wherein $R^1$ represents a 5- or 6-membered heterocyclic group containing one or more nitrogen atoms as said heteroatoms.

6. A pyridylthiazolidine carboxamide derivative or a pharmaceutically acceptable salt thereof as claimed in claim 5 wherein said heterocyclic group is a pyrimidinyl, pyrrolidinyl, pyridyl or imidazolyl group.

7. A pyridylthizolidine carboxamide derivative or a pharmaceutically acceptable salt thereof as claimed in claim 1 wherein $R^1$ represents a 5- or 6-membered heterocyclic group containing an oxygen and/or sulfur atom.

8. A pyridylthiazolidine carboxamide derivative or a pharmaceutically acceptable salt thereof as claimed in claim 7 wherein said heterocyclic group is a furyl or thienyl group.

9. 1-[3-(2-furyl)propyl]-4-[2-(3-pyridyl)thiazolidine-4-ylcarbonyl]piperazine or a pharmaceutically acceptable salt thereof.

10. A pharmaceutical composition having platelet activating factor antagonizing activity and containing, as an active ingredient thereof, said pyridylthiazolidine carboxamide derivative or a pharmaceutically acceptable salt thereof as claimed in any one of claims 1 to 9 and a pharmaceutically acceptable carrier or excipient.

* * * * *